(12) United States Patent
Stojicevic et al.

(10) Patent No.: US 9,995,653 B2
(45) Date of Patent: Jun. 12, 2018

(54) METHOD AND DEVICE FOR DIAGNOSING THE FUNCTION OF AN EXHAUST GAS SENSOR

(71) Applicant: Robert Bosch GmbH, Stuttgart (DE)

(72) Inventors: Dorde Stojicevic, Fellbach (DE); Bastian Roetzler, Markgroeningen (DE); Bernhard Kamp, Tamm (DE); Joerg Bosch, Vaihingen/Enz (DE); Ariel Di Miro, Stuttgart (DE); Ipek Sarac, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 136 days.

(21) Appl. No.: 14/841,772

(22) Filed: Sep. 1, 2015

(65) Prior Publication Data

US 2016/0061691 A1   Mar. 3, 2016

(30) Foreign Application Priority Data

Sep. 1, 2014 (DE) .................. 10 2014 217 402

(51) Int. Cl.
| | |
|---|---|
| *G01M 15/10* | (2006.01) |
| *F02D 41/14* | (2006.01) |
| *G01N 15/06* | (2006.01) |
| *F02D 41/22* | (2006.01) |
| *G01N 15/00* | (2006.01) |

(52) U.S. Cl.
CPC ....... *G01M 15/102* (2013.01); *F02D 41/1466* (2013.01); *F02D 41/1494* (2013.01); *F02D 41/222* (2013.01); *G01N 15/0606* (2013.01); *G01N 15/0656* (2013.01); *F01N 2560/05* (2013.01); *F01N 2900/0416* (2013.01); *G01N 2015/0046* (2013.01); *Y02T 10/40* (2013.01)

(58) Field of Classification Search
CPC .......... F01N 2560/025; F01N 2560/20; F02D 41/1494; F02D 41/1495; F02D 41/1454; F02D 41/1455; F02D 41/222; G01N 27/4067; Y02T 10/47
See application file for complete search history.

(56) References Cited

U.S. PATENT DOCUMENTS

| | | | | |
|---|---|---|---|---|
| 4,611,562 A | * | 9/1986 | Nakano | F02D 41/1494 123/697 |
| 4,724,815 A | * | 2/1988 | Mieno | F02D 41/1495 123/690 |
| 5,447,696 A | * | 9/1995 | Harada | F01N 3/2013 422/108 |

(Continued)

FOREIGN PATENT DOCUMENTS

| | | |
|---|---|---|
| DE | 102007060939 | 6/2009 |
| DE | 102010027975 | 10/2011 |

(Continued)

*Primary Examiner* — David A Rogers
(74) *Attorney, Agent, or Firm* — Michael Best & Friedrich LLP

(57) ABSTRACT

A method for diagnosing the function of an exhaust gas sensor in an exhaust gas. The function is evaluated here according to whether during a heating phase an operating temperature of the exhaust gas sensor has been reached for a predefined time period. It is taken into account here whether during the heating phase sufficient heating power has been available to carry out a successful heating phase.

29 Claims, 3 Drawing Sheets

(56) References Cited

U.S. PATENT DOCUMENTS

| | | | | |
|---|---|---|---|---|
| 5,454,259 | A * | 10/1995 | Ishii | F02D 41/1495 73/114.72 |
| 5,709,198 | A * | 1/1998 | Sagisaka | F02D 41/1455 123/684 |
| 5,811,661 | A * | 9/1998 | Scheid | F02D 41/1495 73/23.32 |
| 6,294,075 | B1 * | 9/2001 | Poggio | F02D 41/1496 123/697 |
| 6,314,790 | B1 * | 11/2001 | Sagisaka | F02D 41/1455 73/23.31 |
| 6,386,021 | B1 * | 5/2002 | Carr | F02D 41/221 73/114.73 |
| 6,681,563 | B2 * | 1/2004 | Glugla | F01N 3/101 123/198 F |
| 7,779,626 | B2 * | 8/2010 | Ohsaki | F02D 41/0072 60/276 |
| 8,148,995 | B2 * | 4/2012 | Hashimoto | F02D 41/1494 324/511 |
| 2001/0054608 | A1 * | 12/2001 | Ohkuma | F02D 41/1494 219/205 |
| 2002/0000436 | A1 * | 1/2002 | Hashimoto | G01N 27/122 219/497 |
| 2007/0073470 | A1 * | 3/2007 | Watanabe | F02D 41/062 701/113 |
| 2008/0041134 | A1 * | 2/2008 | Hattori | G01N 27/4175 73/1.06 |
| 2008/0116071 | A1 * | 5/2008 | Nakamura | G01N 27/4175 204/427 |
| 2008/0128277 | A1 * | 6/2008 | Fukuda | G01N 27/4175 204/401 |
| 2009/0278548 | A1 * | 11/2009 | Hashimoto | F02D 41/1494 324/511 |
| 2011/0252768 | A1 | 10/2011 | Baumann et al. | |
| 2011/0265551 | A1 * | 11/2011 | Hopka | F01N 3/021 73/23.31 |
| 2011/0296818 | A1 * | 12/2011 | Hashimoto | F02D 41/1494 60/286 |
| 2016/0123842 | A1 * | 5/2016 | Yoo | F02D 41/1494 73/1.06 |

FOREIGN PATENT DOCUMENTS

| | | | | |
|---|---|---|---|---|
| EP | 0827854 | A2 * | 3/1998 | B60H 1/2206 |
| JP | 63079049 | A * | 4/1988 | F02D 41/1494 |
| JP | 01232143 | A * | 9/1989 | |
| JP | 2008139241 | A * | 6/2008 | |

* cited by examiner

METHOD AND DEVICE FOR DIAGNOSING THE FUNCTION OF AN EXHAUST GAS SENSOR

BACKGROUND OF THE INVENTION

The invention relates to a method for diagnosing the function of an exhaust gas sensor in an exhaust gas, wherein the exhaust gas is at least temporarily brought to an operating temperature during a heating phase by heating with an electric heater.

The invention also relates to a device for carrying out the method.

Exhaust gas sensors are used, for example, in the form of particle sensors for on-board diagnosis of particle filters in the exhaust gas of internal combustion engines. For this purpose, the exhaust gas is fed past an electrode structure of the particle sensor and the change in the impedance between the electrodes as a result of the particles accumulated from the exhaust gas is evaluated.

Such a particle sensor is known, for example, from document DE 10 2007 060 939 A1. Two interdigital electrodes which engage one in the other are applied to an insulating carrier and form the sensor element which is connected to a control device. During a measuring phase, soot is deposited on the electrodes. The particle content of the exhaust gas can be determined from the chronological profile of the change in impedance which is brought about thereby. If the particle sensor is loaded with soot to such an extent that a further change in impedance no longer takes place, said soot is burnt off during a regeneration phase. During this heating phase, the particle sensor is heated using an integrated heating element.

During the regeneration it is known to determine the temperature of the particle sensor using an integrated temperature sensor and to set it using a heating regulator.

Step DE 10 2010 027 975 A1 describes a method for self-diagnosis of an exhaust gas probe which has a heating element, wherein the exhaust gas probe can be a particle sensor. In order to diagnose the exhaust gas probe, the measured heating power of the heating element is compared with a modeled heating power. In the event of a deviation which is greater than a predefined value, the exhaust gas probe is detected as being faulty. The self-diagnosis permits defective particle sensors whose electrodes have been damaged to be detected and corresponding visual or audible warning signals to be emitted.

An object of the invention is to make available a method with which the function of an exhaust gas sensor can be detected easily and reliably.

It is furthermore an object of the invention to make available a device for carrying out the method.

SUMMARY OF THE INVENTION

The object of the invention which relates to the method for diagnosing the function of an exhaust gas sensor is achieved in accordance with the invention by virtue of the fact that a faulty exhaust gas sensor is inferred if during a heating phase a predefined operating temperature of the exhaust gas sensor is not reached or if the predefined operating temperature is not reached for a predefined time period. The heating phase can be provided, for example, for carrying out regeneration of the exhaust gas sensor. If the operating temperature is not reached or is not reached for a sufficiently long time, the regeneration cannot be carried out successfully and a subsequent measuring phase can be started. The heating phase can be provided, for example, for regenerating an accumulating particle sensor. During a preceding measuring phase particles accumulated at the particle sensor are burnt here during the heating phase. If the temperature which is required to burn off the particle sensor is not reached or is not reached for a sufficiently long time period, at least some of the accumulated particles are not reliably burnt, with the result that the measuring capability of the particle sensor is not brought about. This can easily be monitored by using a temperature sensor and measuring the time. If the required temperature cannot be set, or cannot be set for a sufficiently long time, a fault in the exhaust gas sensor, for example an increased resistance at the heater feed lines or an aged or damaged heater, can be inferred.

Functional testing of the exhaust gas sensor which is easy to implement can be ensured in that a measuring phase following the heating phase is not started if the predefined operating temperature is not reached during the heating phase or is not reached for the predefined time period, and in that a faulty exhaust gas sensor is inferred if the measuring phase following the heating phase is not started. If an operating strategy of an exhaust gas sensor provides that a measuring phase takes place after a heating phase only when the necessary temperature for the predefined time period has been reached during the heating phase, a fault of the exhaust gas sensor can be inferred from a measuring phase which has not started.

The object of the invention with respect to the diagnosis of the function of a heated exhaust gas sensor is also achieved according to the invention in that a necessary heating power for reaching the operating temperature is determined, in that an available heating power for reaching the operating temperature is determined, in that a diagnosis for the detection of an intact or defective exhaust gas sensor is carried out if the available heating power during the heating phase was continuously greater than the necessary heating power or if the available heating power during the heating phase was continuously greater than the necessary heating power by a predefined threshold value, and in that the diagnosis is not carried out if the available heating power during the heating phase was at least temporarily lower than the required necessary heating power or if the available heating power was at least temporarily lower than the sum of the heating power and the threshold value. Under unfavorable conditions, for example in the case of an excessively low supply voltage and in the case of excessive cooling of the exhaust gas sensor, it may be the case that the operating temperature cannot be reached or cannot be reached for the predefined time period, since the available heating power is not sufficient for this. By comparing the necessary heating power with the available heating power it is possible to check whether during the heating phase sufficient heating power had been available to reach the operating temperature under the given conditions. If this is not the case, it cannot be decided whether the exhaust gas sensor is intact or defective. Correspondingly, after a heating phase with an excessively low available heating power, no diagnosis as to whether the exhaust gas sensor is intact or defective takes place. If, on the other hand, sufficient heating power was available, the diagnosis is carried out. In this way it is possible to prevent intact exhaust gas sensors being erroneously diagnosed as faulty.

In order to be able to compare the heating power necessary during the heating phase and the available heating power, they must be determined with sufficient accuracy. For this purpose it is possible to provide that the necessary heating power is determined from a characteristic diagram at least as a function of an exhaust gas speed and an exhaust gas temperature, or in that the necessary heating power is determined from a physical model at least as a function of a thermal conductivity coefficient or a temperature of the exhaust gas sensor or a wall temperature of an exhaust gas duct or the exhaust gas speed or the exhaust gas temperature or a thermal irradiation coefficient, individually in each case or in combination of at least two of the variables, and/or in that the available heating power is determined from an available supply voltage of the heater or from the available supply voltage multiplied by a maximum duty cycle or from a limit, predefined by a control device, of the supply voltage. It can advantageously be provided here that the necessary heating power and/or the available heating power are determined for a borderline exhaust gas sensor with a heating power requirement which is just still permissible. The heating powers are therefore determined for a limit sample and not for the exhaust gas sensor which is actually present. If the available heating power is sufficient to carry out the heating phase for such a borderline exhaust gas sensor, it is also sufficient for a better exhaust gas sensor.

A simple procedure for deciding whether the available heating power is sufficient to make available a necessary heating power can be achieved by virtue of the fact that the comparison between the available heating power and the necessary heating power is carried out on the basis of a first quotient of the available heating power and the necessary heating power or on the basis of a second quotient of the necessary heating power and the available heating power as a comparison variable, or in that the comparison is carried out on the basis of a first difference between the available heating power and the necessary heating power or on the basis of a second difference between the necessary heating power and the available heating power as a comparison variable. The comparison variables can be determined from the necessary and available heating powers without a large degree of mathematical complexity. Said comparison variables permit a direct comparison as to whether the available heating power is greater than the necessary heating power or greater than the sum of the necessary heating power and the threshold value. For this purpose, it is possible to require, for example for the second quotient of the necessary heating power and the available heating power as a comparison variable that said quotient must assume a value of less than one in order to start a diagnosis. If the value is above one, the necessary heating power is greater than the available heating power, and the diagnosis as to whether or not the exhaust gas sensor is faulty is suppressed.

In order to take into account changes in the necessary heating power and the available heating power during the heating phase it can be provided that during a heating phase or a time segment of the heating phase the minimum first quotient which occurs or the greatest second quotient which occurs or the minimum first difference which occurs or the greatest second difference which occurs is determined, and in that a diagnosis for the detection of an intact or defective exhaust gas sensor is carried out if the minimum first quotient which occurs or the minimum first difference which occurs is greater than a respective predefined value or if the greatest second quotient which occurs or the greatest second difference which occurs is lower than a respective predefined value. It is therefore possible to test whether the necessary heating power could not have been made available, at least for a certain time, during the heating phase. An available heating power which is too low only temporarily can also bring about a situation in which the necessary operating temperature cannot be reached or cannot be reached over the predefined time period. In such a case, it can therefore be provided that the diagnosis is not carried out. The specified time segment of the heating phase can be, for example, the duration of a burn-off phase during the regeneration of a particle sensor.

According to an alternative refinement variant of the invention, it can be provided that for the comparison of the available heating power and the necessary heating power, instead of the heating power itself, a heating power variable which is associated with the heating power, in particular a heater effective voltage, a square of the heater effective voltage, a heater duty cycle or an output heating power, is used. The variables correlate with the heating power and can therefore be correspondingly used for the evaluation. This may be advantageous, in particular, when the variable used is already present for other applications in a control unit and can also be used for the comparison of the available heating power and the necessary heating power. Furthermore it is conceivable that in the case of respectively present electronic wiring of the exhaust gas sensor, some of the variables are easier to sense than the heating power itself.

Simple detection of a faulty exhaust gas sensor and of an intact exhaust gas sensor can be achieved by virtue of the fact that a defective exhaust gas sensor is inferred if
a) during a heating phase a predefined operating temperature is not reached or if the predefined operating temperature is not reached for a predefined time period or if a measuring phase following the heating phase is not started and if
b) the available heating power during the heating phase was continuously greater than the necessary heating power or if the available heating power during the heating phase was continuously greater than the necessary heating power by the predefined threshold value, and/or in that an intact exhaust gas sensor is inferred if
a) during a heating phase a predefined operating temperature is reached or if the predefined operating temperature is reached for a predefined time period or if a measuring phase following the heating phase is started and if
b) the available heating power during the heating phase was continuously greater than the necessary heating power or if the available heating power during the heating phase was continuously greater than the necessary heating power by the predefined threshold value, and/or in that no diagnosis of the exhaust gas sensor takes place if the available heating power during the heating phase was at least temporarily less than the necessary heating power or if the available heating power was at least temporarily less than the sum of the necessary heating power and the predefined threshold value.

An evaluation as to whether an exhaust gas sensor is defective or intact is accordingly performed only if sufficient heating power has been available during the heating phase to cover the necessary heating power. The attainment of the predefined operating temperature for the predefined time period is used as the criterion as to whether the exhaust gas sensor is defective or intact. If the available heating power was insufficient during the heating phase, no diagnosis is carried out. An incorrect diagnosis, during which an intact exhaust gas sensor is categorized as defective or a defective exhaust gas sensor is categorized as intact, can therefore be reliably avoided.

In accordance with a further embodiment variant of the invention there can be provision that a defective exhaust gas sensor is inferred if
a) during a heating phase a predefined operating temperature is not reached or if the predefined operating temperature is not reached for a predefined time period or if a measuring phase following the heating phase is not started and if
b) the available heating power during the heating phase was continuously greater than the necessary heating power or if the available heating power during the heating phase was continuously greater than the necessary heating power by a predefined first threshold value, and/or in that an intact exhaust gas sensor is inferred if
a) during a heating phase a predefined operating temperature is reached or if the predefined operating temperature is reached for a predefined time period or if a measuring phase following the heating phase is started and if
b) the available heating power during the heating phase was at least temporarily lower than the necessary heating power or if the available heating power during the heating phase was at least temporarily lower than the sum of the necessary heating power and a second threshold value which is lower compared to the first threshold value, and/or in that no diagnosis of the exhaust gas sensor takes place if
a) during a heating phase a predefined operating temperature is not reached or if the predefined operating temperature is not reached for a predefined time period or if a measuring phase following the heating phase is not started and if
b) the available heating power during the heating phase was at least temporarily lower than the necessary heating power or if the available heating power was at least temporarily lower than the sum of the necessary heating power and the first threshold value, and/or in that no diagnosis of the exhaust gas sensor takes place if
during a heating phase a predefined operating temperature is reached or if the predefined operating temperature is reached for a predefined time period or if a measuring phase following the heating phase is started and if the available heating power during the heating phase was continuously greater than the necessary heating power or if the available heating power during the heating phase was continuously greater than the sum of the necessary heating power and the second threshold value.

A defective exhaust gas sensor is accordingly detected only if the heating phase has not been successfully concluded and at the same time sufficient heating power has been available during the heating phase to reach the operating temperature. If only insufficient heating power was available, this can also be the cause of the unsuccessfully ended heating phase. In order to avoid an actually intact exhaust gas sensor being evaluated as defective under such unfavorable conditions during the heating phase, when there is insufficient heating power, the diagnosis for a defective exhaust gas sensor is not carried out.

In contrast, an intact exhaust gas sensor is detected only if the heating phase has been successfully concluded when there is a comparatively low available heating power. This procedure takes into account the fact that even an actually borderline exhaust gas sensor can be successfully regenerated under favorable conditions. Such an actually defective exhaust gas sensor would be evaluated as being intact in the case of a successfully concluded heating phase. In order to avoid this, testing for intactness is carried out only if the available heating power is lower than the necessary heating power or lower than the necessary heating power plus a predefined second threshold value.

According to a further embodiment variant of the invention, there can be provision that when diagnosis is carried out and an exhaust gas sensor is detected as being defective after a first heating phase, an entry is made in a fault memory, and in that the entry in the fault memory is reset if during a following heating phase a predefined operating temperature is reached and/or if the predefined operating temperature is reached for a predefined time period and/or if a measuring phase following the heating phase is started and if a determined comparison variable during the following heating phase yields a ratio between the necessary heating power and the available heating power, which is less favorable compared to the first heating phase. The comparison variable is formed here, for example, by the first or second quotients or the first or second differences. If less heating power was available compared to the respectively necessary heating power during the following successful heating phase in relation to the first, unsuccessful heating phase and it was therefore possible to carry out the heating phase successfully under unfavorable conditions, the fault entry is deleted and the exhaust gas sensor is categorized as intact. If, on the other hand, more favorable conditions for reaching the operating temperature were present during the subsequent successful heating phase, the fault is not reset. It is therefore ensured that a successful fault entry can subsequently be checked once more and corrected. This avoids an exhaust gas sensor which has previously been categorized as faulty being subsequently found to be intact if a following heating phase occurs successfully only on the basis of significantly more favorable conditions, for example in the case of a relatively high supply voltage or a relatively high exhaust gas temperature.

The method can preferably be applied for monitoring a particle sensor at which particles from the exhaust gas are accumulated during a measuring phase, and the quantity of said particles is determined, and in which method the particles are burnt during a heating phase by heating the particle sensor by means of the electric heater.

The object of the invention relating to the device is achieved in that the control device has a processing device which prevents a transition into a measuring phase after a regeneration phase if the burn-off temperature or the burn-off duration was not reached during the regeneration phase, in that the processing device has means for determining and for comparing a necessary heating power and an available heating power during a regeneration, in that the processing device is configured to enable and carry out a diagnosis of the particle sensor if the available heating power during the regeneration was greater than the necessary heating power or greater than a threshold value above the necessary heating power, in that the processing device is configured not to enable or carry out a diagnosis of the particle sensor if the available heating power during the regeneration was lower than the necessary heating power or lower than the threshold value above the necessary heating power, in that the processing device is configured to diagnose a defective particle sensor if the transition into the measuring phase was prevented and the diagnosis was enabled and/or in that the processing device is configured to diagnose an intact particle sensor if the transition into the measuring phase has taken place and the diagnosis has been enabled. The device carries out a diagnosis of the function of the particle sensor accordingly only when, during the regeneration, sufficient heating power has also actually been available to be able to carry out the regeneration successfully. If this is not the case, the diagnosis is not carried out, since it cannot be decided without doubt whether the particle sensor is defective or intact.

Furthermore, it can be provided that the processing device infers a defective particle sensor if the regeneration has not been concluded successfully and the available heating power during the regeneration was not continuously the same or greater than the necessary heating power or if the available heating power was not continuously greater than the sum of the necessary heating power and a first threshold value, in that the processing device infers an intact particle sensor if the regeneration has been concluded successfully and the available heating power during the regeneration was at least temporarily lower than or equal to the necessary heating power or if the available heating power during the regeneration was at least temporarily lower than a sum of the necessary heating power and a second threshold value, and in that in all other cases the processing device does not carry out any diagnosis of the function of the particle sensor. In this embodiment variant, defect testing is accordingly carried out only when sufficient heating power has been available during the regeneration. Testing of the particle sensor for intactness is, on the other hand, carried out only when the available heating power was rather low compared to the necessary heating power.

BRIEF DESCRIPTION OF THE DRAWINGS

The invention will be explained in more detail below on the basis of an exemplary embodiment illustrated in the figures, of which.

DETAILED DESCRIPTION

Figure 1:
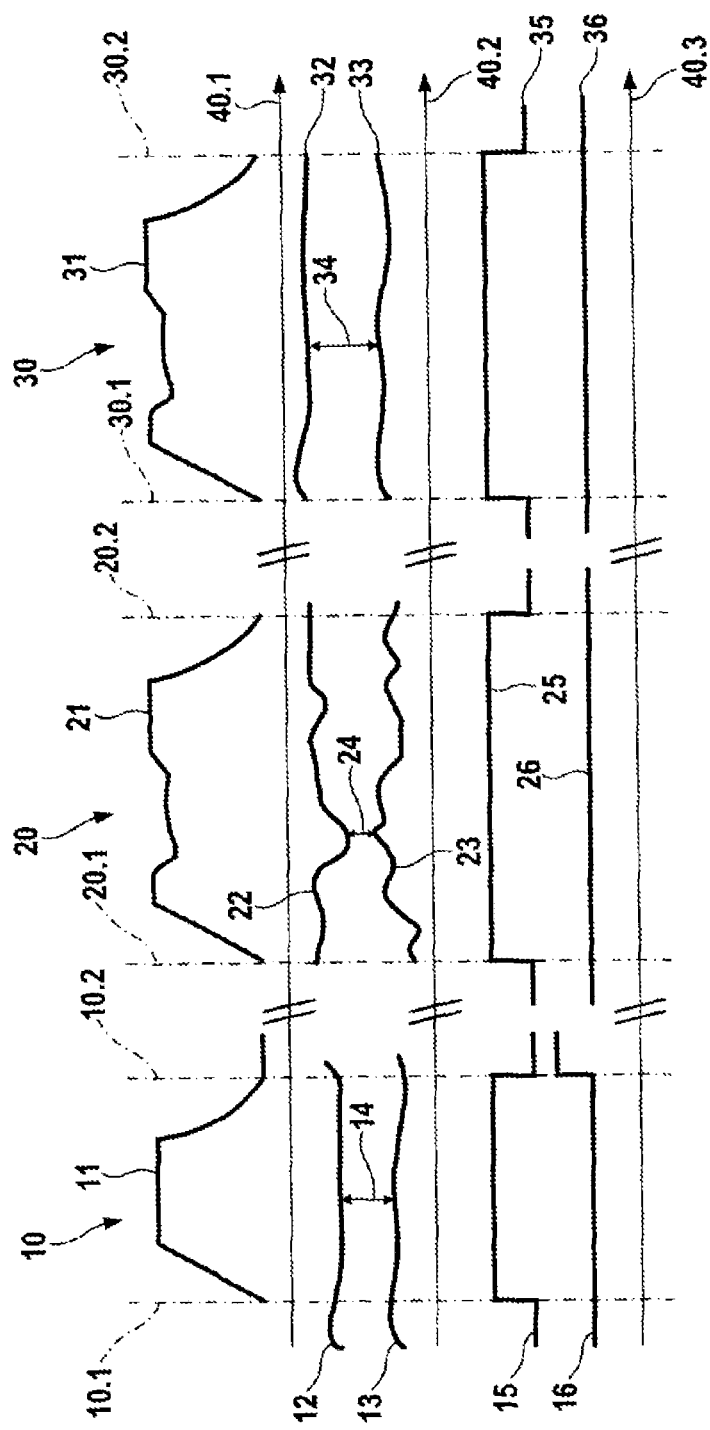
FIG. 1 shows signal profiles during three regeneration phases of a particle sensor in diagram form.

FIG. 1 shows signal profiles during three regeneration phases (10, 20, 30) of a particle sensor in diagram form. The signal profiles of the three regeneration phases (10, 20, 30) are plotted here against three time axes (40.1, 40.2, 40.3) with the same time divisions.

The regeneration phases (10, 20, 30) represent heating phases in which the exhaust gas sensor which is embodied as a particle sensor is heated to an operating temperature. The duration of a first regeneration phase 10 is bounded by a first mark 10.1 and a second mark 10.2, that of a second regeneration phase 20 by a third mark 20.1 and a fourth mark 20.2, and that of a third regeneration phase 30 by a fifth mark 30.1 and a sixth mark 30.2.

During the first regeneration phase 10, the temperature of the particle sensor varies in accordance with a first temperature profile 11. Here, said temperature initially increases during a heating phase, then remains constant at a predefined operating temperature during a burn-off phase and drops again in a cooling phase after the burn-off phase. In the diagram under the first temperature profile 11, the profiles of a first available heating power 12 and of a first necessary heating power 14 during the first regeneration phase 10 are given. The minimum first difference A 14 between the first available heating power 12 and the first necessary heating power 13 is marked by a double arrow. A first regeneration status 15 and a first measuring phase status 16 are represented as internal binary control signals of a control device underneath the first heating powers 12, 13.

The particle sensor (not illustrated) is embodied as an accumulating, resistive particle sensor with an interdigital electrode structure, parts of which engage one in the other in a comb-like fashion. During a measuring phase, particles accumulate on the electrode structure from an exhaust gas and change the impedance of said electrode structure. The particle content of the exhaust gas can be inferred from the chronological profile of the change in the impedance. If the particle sensor is loaded with particles, it must be burnt-off before a subsequent measuring phase. This is done by means of the illustrated increase in the temperature during the regeneration phases 10, 20, 30. The increase in temperature is brought about by an electric heater which is integrated in the particle sensor and which is actuated by means of a heating regulator in such a way that the particle sensor assumes the operating temperature. A temperature sensor is assigned to the particle sensor for this purpose.

The start of the first regeneration phase 10 takes place at the first mark 10.1 by means of a jump of the first regeneration status 15 from low to high. Starting from this time, the heater heats the particle sensor until it has reached the operating temperature. The heating regulator then regulates the heating power fed to the heater by setting a duty cycle to a pulse-width modulation in such a way that the operating temperature is maintained during the burn-off phase. If the operating temperature has been maintained for a predefined time period, the burn-off phase is ended and the temperature drops. The end of the first regeneration phase 10 is reached at the changeover of the first regeneration status 15 from high to low.

During the first regeneration phase 10, the profile of the first available heating power 12 and of the first necessary heating power 13 is determined. At the same time, the minimum first difference A 14 is determined by forming the difference between the first available heating power 12 and the first necessary heating power 13 by means of the profile of the first regeneration phase 10, and filtering out the minimum difference.

The representation of the second regeneration phase 20 corresponds to the first regeneration phase 10 with a second temperature profile 21, a second available heating power 22, a second necessary heating power 23, the minimum first difference B 24, a second regeneration status 25 and a second measuring phase status 26. A third temperature profile 31, a third available heating power 32, a third necessary heating power 33, the minimum first difference C 34, a third regeneration status 35 and a third measuring phase status 36 are correspondingly represented for the third regeneration phase 30.

During the first regeneration phase 10, the first temperature profile 11 extends to the operating temperature during the burn-off phase. Successful regeneration of the particle sensor is therefore assumed, with the result that at the end of the first regeneration phase 10, the first measuring phase status jumps from low to high and therefore enables a successful measuring phase. At the same time, the minimum first difference A remains greater than a threshold value (not illustrated). This means that sufficient heating power 12 was available for the regeneration of the particle sensor. According to the invention, the execution of a diagnosis for the detection of an intact or defective particle sensor is as a result enabled. This diagnosis checks whether the first measuring phase status 16 after the first regeneration phase 10 changes from low to high and therefore the first following measuring phase was started. If this is the case, as shown in the exemplary embodiment for the first regeneration phase 10, the particle sensor is evaluated as intact.

During the second regeneration phase 20, the operating temperature is not reached for the predefined time period, as is apparent from the second temperature profile 21. Therefore, the second measuring phase status 26 does not change from low to high after the second regeneration phase 20, and a following measuring phase is not started. However, at the same time the minimum first difference B 24 remains below the predefined threshold value. Accordingly, there was not sufficient heating power available during the second regeneration phase 20 to adjust the temperature of the particle sensor to the operating temperature. For this reason, the diagnosis for the detection of an intact or defective particle sensor is not carried out, since it cannot be proven without doubt whether the unsuccessful regeneration is due to a defect in the particle sensor or to the insufficient second available heating power 22.

The operating temperature is not reached for the predefined time period during the third regeneration phase 30 either, for which reason the third measuring phase status 36 does not change from low to high and therefore the following measuring phase is not started. As is shown by the minimum first difference C 34 which is above the threshold value (not illustrated), during the regeneration phase 30, sufficient available heating power 32 was made available to provide the third necessary heating power 33. The diagnosis for the detection of an intact or defective particle sensor is therefore enabled and carried out. The diagnosis detects that the third measuring phase status 36 is not at high and the following measuring phase was therefore not started, and therefore the diagnosis detects a defective particle sensor.

The diagnosis accordingly tests whether sufficient heating energy was available to carry out a successful regeneration. If this is the case and the regeneration was nevertheless not successful, a defective particle sensor is inferred. On the other hand, if the regeneration was successful, an intact particle sensor is diagnosed. The available heating power 12, 22, 32 and the necessary heating power 13, 23, 33 are not determined for the present particle sensor but rather for a limit sample which is still in fact to be considered as being intact with a heating power requirement which is still just permissible.

Figure 3:
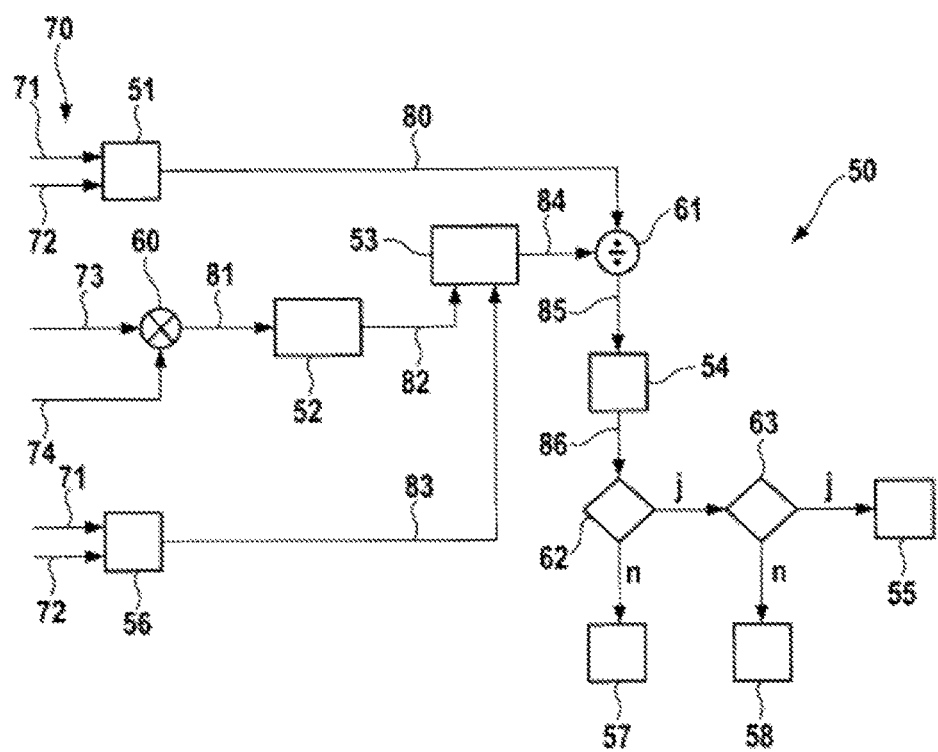
FIG. 3 shows a flowchart relating to the enabling of a diagnosis of the function and the detection of the function of a particle sensor.

In addition to the illustrated first difference 14, 24, 34, a second difference between the necessary heating power 13, 23, 33 and the available heating power 12, 22, 32, a first quotient of the available heating power 12, 22, 32 and the necessary heating power 13, 23, 33 or a second quotient 85, as shown in FIG. 3, of the necessary heating power 13, 23, 33 and the available heating power 12, 22, 32 can also be used as a comparison variable for determining whether sufficient heating power was available for carrying out the regeneration. The decision as to whether sufficient heating power was available for enabling the diagnosis can be defined here starting from an equilibrium between the available heating power 12, 22, 32 and the necessary heating power 13, 23, 33, that is to say in the case of the first differences 14, 24, 34 or second differences starting from 0 or in the case of first quotients or second quotients starting from 1. Alternatively, differences or quotients which differ from 0 or 1 can be predefined, with the result that the available heating power 12, 22, 32 must be above the necessary heating power 13, 23, 33, in accordance with a predefined threshold value. The enabling of the diagnosis can also take place after a direct comparison of the necessary heating power 13, 23, 33 and the available heating power 12, 22, 32 if the necessary heating power 13, 23, 33 is lower than the available heating power 12, 22, 32.

Figure 2:
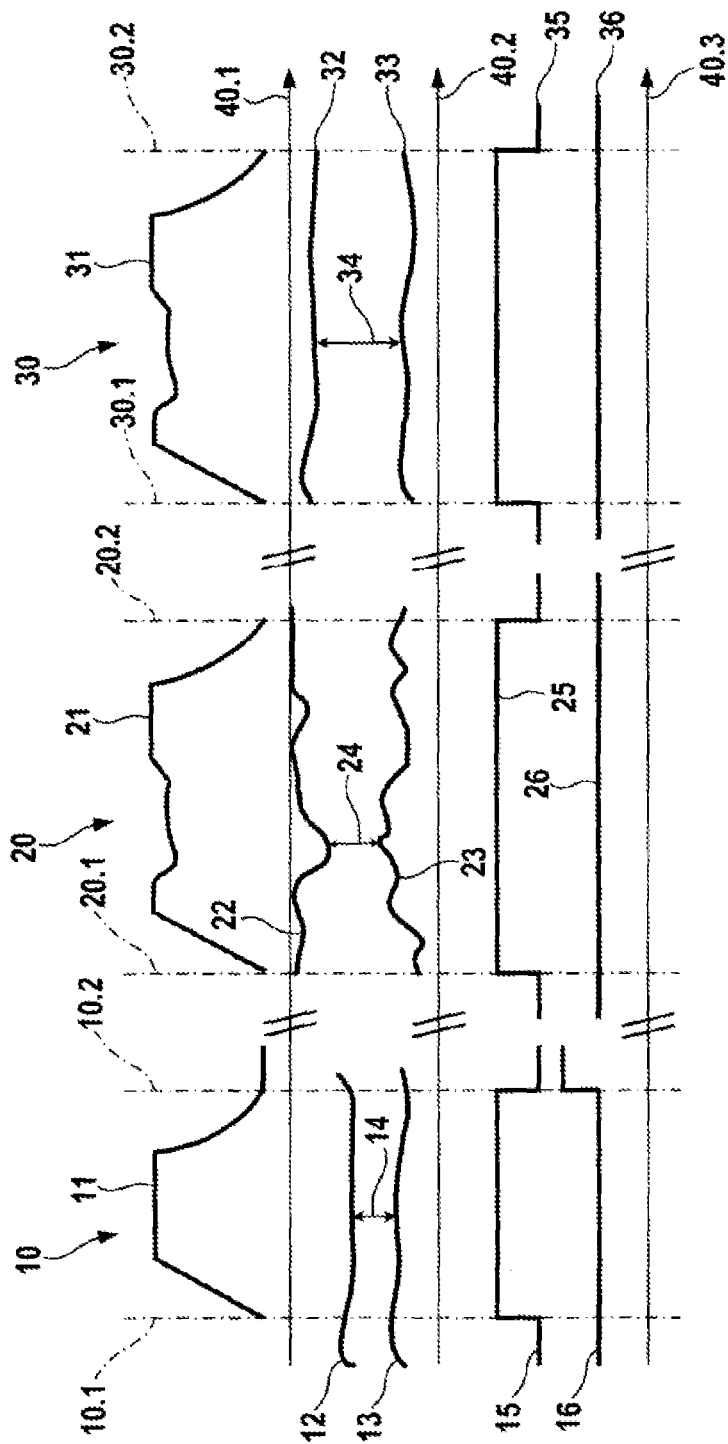
FIG. 2 shows the signal profiles from FIG. 1 during three further regeneration phases of a particle sensor in diagram form.

FIG. 2 shows the signal profiles from FIG. 1 during three further regeneration phases of a particle sensor in diagram form. Identical signals and diagram axes are designated in the same way as were introduced for FIG. 1.

The second regeneration phase 20 and the third regeneration phase 30 correspond in their signal profiles and the associated evaluation to the corresponding regeneration phases 20, 30 from FIG. 1.

According to the alternative evaluation illustrated in FIG. 2, an evaluation of a particle sensor as intact takes place only when the regeneration phase has been successfully concluded and the following measuring phase has been started, and at the same time only a small first available heating power 12 compared to the first necessary heating power 13 has been determined. This is apparent in the comparatively small minimum first difference A 14 which is below a second threshold value (not illustrated). If it was possible to carry out a successful regeneration with a changeover into a following measuring phase under these comparatively unfavorable conditions, it can reliably be assumed that there is an intact particle sensor. Such a successful regeneration of the real particle sensor is also possible under these conditions since the necessary heating power 13, 23, 33 is determined for a limit sample and not for the actually present particle sensor. According to this alternative evaluation, no evaluation of the particle sensor as intact takes place under the conditions shown in FIG. 1 for the first regeneration phase 10, since here the minimum first difference A 14 is above the second threshold value (not illustrated). Under these favorable conditions, a particle sensor which is just no longer acceptable (BPU: best part unacceptable) could also still be regenerated successfully. The alternative evaluation method described in FIG. 2 therefore prevents a defective particle sensor from being evaluated as intact owing to favorable regeneration conditions.

FIG. 3 shows a flowchart 50 relating to the enabling of a diagnosis of the function and to the detection of the function of a particle sensor with the input variables 70 of exhaust gas temperature 71, exhaust gas speed 72, supply voltage 73 and maximum duty cycle 74. The flowchart 50 is formed from eight blocks 51, 52, 53, 54, 55, 56, 57, 58, a multiplication point 60, a division point 61 and two comparison blocks 62, 63, and is implemented as software and hardware in a control device.

The exhaust gas temperature 71 and the exhaust gas speed 72 are fed to the first block 51 and the sixth block 56, while the supply voltage 73 and the maximum duty cycle 74 are fed to the multiplication point 60. In the first block 51, a necessary heating power 80 is formed which is passed onto a division point 61. For this purpose, a characteristic diagram, from which the necessary heating power 80 is formed from the exhaust gas temperature 71 and the exhaust gas speed 72, is stored in the first block 51. Alternatively to this, a model, which determines the necessary heating power $P_{erf}$ 80 on the basis of a thermal conductivity coefficient Kc, the temperature of the particle sensor Ts, a modeled wall temperature Tw of an exhaust gas duct, a thermal convection characteristic diagram f( ) as a function of the exhaust gas speed 72 vEG and the exhaust gas temperature 71 TEG and a thermal irradiation coefficient Kr in accordance with the equation $$P_{erf} = Kc*(Ts-Tw) + f(vEG, TEG)*(Ts-TEG) + Kr*Ts^4$$

can be stored in the first block 51.

An effective supply voltage 73 is formed at the multiplication point 60 by multiplying the available supply voltage 73 of the heater, for example of a battery voltage, and the maximum duty cycle 74 which can be set. The heating power of the heater is set by means of the duty cycle. Given a maximum duty cycle 74, the maximum possible effective supply voltage 81 is obtained for the available supply voltage 73, from which effective supply voltage 81 a first effective heating power 82 is formed in the second block 52 by squaring and dividing by the electric resistance of the heater. In the sixth block 56, a second effective heating power 83 is determined as a function of additional limits which are provided and which are based, for example, on the control device which actuates the heater. Such limits can be a maximum permissible heating voltage or power limits of the control device itself. The second effective heating power 83 is determined here using a model composed of the exhaust gas temperature 71 and the exhaust gas speed 72. In the third block 53, the respective smaller value of the first effective heating power 82 and the second effective heating power 83 is determined and output as an available heating power 84. As a result, the influencing factor (supply voltage 73 and maximum duty cycle 74 or power limits of the control device) which actually limits the power is reliably taken into account during the determination of the available heating power 84. By dividing the necessary heating power 80 by the available heating power 84, the second quotient 85 V is formed at the division point 61. In the fourth block 54, the largest, second quotient 86 $V_{max}$ is filtered out from said second quotient 85 V in the course of a regeneration and fed to the first comparison block 62. It is tested here whether the largest, second quotient 86 $V_{max}$ assumes a value of less than one, and therefore the available heating power 84 was always larger than the necessary heating power 80 during the regeneration. If this is not the case, a diagnosis as to whether the particle sensor is intact or defective is not carried out and the sequence ends in the seventh block 57. If the largest, second quotient 86 $V_{max}$ is less than one, there was sufficient heating power available for carrying out the regeneration and the sequence jumps to the second comparison block 63. Here, the interrogation occurs as to whether the regeneration was successfully concluded, that is to say whether the measuring phase status 16, 26, 36 shown in FIG. 1 has started the following measuring phase. If this is the case, an intact particle sensor is assumed and the sequence is ended in the fifth block 55. If, on the other hand, the regeneration was not successfully concluded and a following measuring phase was not started, a defective particle sensor is assumed. Then, in the eighth block 58, a corresponding fault entry is made in a fault memory and information is issued to an operator of the particle sensor, for example the driver of a motor vehicle.

The detection as to whether or not a fault is present in the particle sensor occurs according to the invention in that it is checked whether during the regeneration phase a predefined operating temperature of the particle sensor is not reached or whether the predefined operating temperature is not reached for a predefined time period. This can be detected from whether a measuring phase following the regeneration is started, as is described for the second comparison block 63. Furthermore, the invention provides for checking as to whether sufficient heating power was available to carry out successful regeneration. Checking of the functional capability of the particle sensor is enabled only if this is the case.

The method very largely avoids intact particle sensors, in which regeneration has not proceeded successfully owing to external circumstances, from being erroneously categorized as defective. Nevertheless, if such an erroneous fault entry is made in the fault memory, there is the possibility of correction, which is not shown in the flowchart 50. If a regeneration with a defect message is followed by a further successful regeneration of the particle sensor, it is checked whether the regeneration conditions during the further successful regeneration were less favorable than during the regeneration with the defect message, that is to say whether the ratio between the necessary heating power 80 and the available heating power 84 has become worse. If it was possible to regenerate the particle sensor under such unfavorable conditions, the previously made fault entry is deleted. In order to carry out this error recovery, it is advantageous if the comparison between the necessary heating power 80 and the available heating power 84 does not occur over the entire duration of the regeneration phase 10, 20, 30 but rather only during the burn-off phase.

The invention claimed is:

1. A method for diagnosing the function of an exhaust gas sensor in an exhaust gas, wherein the exhaust gas sensor is at least temporarily brought to an operating temperature during a heating phase by heating with an electric heater, comprising inferring a faulty exhaust gas sensor if during the heating phase a predefined operating temperature of the exhaust gas sensor is not reached or if the predefined operating temperature is not reached for a predefined time period; wherein when the exhaust gas sensor is not inferred to be faulty, regeneration of the exhaust gas sensor is performed, wherein when diagnosis is carried out and an exhaust gas sensor is detected as being defective after a first heating phase, an entry is made in a fault memory, and in that the entry in the fault memory is reached if during a following heating phase a predefined operating temperature is reset and/or if the predefined operating temperature is reached for a predefined time period and/or if a measuring phase following the heating phase is started and if a determined comparative variable during the following heating phase yields a ratio between the necessary heating power (13, 23, 33, 80) and the available heating power (12, 22, 32, 84), which is less favourable compared to the first heating phase.

2. The method according to claim 1, characterized in that a measuring phase following the heating phase is not started if the predefined operating temperature is not reached during the heating phase or is not reached for the predefined time period, and in that a faulty exhaust gas sensor is inferred if the measuring phase following the heating phase is not started.

3. The method according to claim 1, characterized in that a defective exhaust gas sensor is inferred if
    a) during a heating phase a predefined operating temperature is not reached or if the predefined operating temperature is not reached for a predefined time period or if a measuring phase following the heating phase is not started and if
    b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that an intact exhaust gas sensor is inferred if
    a) during a heating phase a predefined operating temperature is reached or if the predefined operating temperature is reached for a predefined time period or if a measuring phase following the heating phase is started and if
    b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or in that no diagnosis of the exhaust gas sensor takes place if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the predefined threshold value.

4. The method according to claim 1, characterized in that a defective exhaust gas sensor is inferred if
  a) during a heating phase (10, 20, 30) a predefined operating temperature is not reached or if the predefined operating temperature is not reached for a predefined time period or if a measuring phase following the heating phase is not started and if
  b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined first threshold value, and/or
in that an intact exhaust gas sensor is inferred if
  a) during a heating phase a predefined operating temperature is reached or if the predefined operating temperature is reached for a predefined time period or if a measuring phase following the heating phase is started and if
  b) the available heating power (12, 22, 32, 84) during the heating phase was at least temporarily lower than the necessary heating power (13, 23, 33, 80) or if the available heating power (12, 22, 32, 84) during the heating phase was at least temporarily lower than the sum of the necessary heating power (13, 23, 33, 80) and a second threshold value which is lower compared to the first threshold value, and/or
in that no diagnosis of the exhaust gas sensor takes place if
  a) during a heating phase a predefined operating temperature is not reached or if the predefined operating temperature is not reached for a predefined time period or if a measuring phase following the heating phase is not started and if
  b) the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the first threshold value, and/or
in that no diagnosis of the exhaust gas sensor takes place if
  a) during a heating phase a predefined operating temperature is reached or if the predefined operating temperature is reached for a predefined time period or if a measuring phase following the heating phase is started and if
  b) the available heating power (12, 22, 32, 84) during the heating phase was continuously greater than the necessary heating power (13, 23, 33, 80) or if the available heating power (12, 22, 32, 84) during the heating phase was continuously greater than the sum of the necessary heating power (13, 23, 33, 80) and the second threshold value.

5. The method according to claim 1, wherein the method is used for monitoring a particle sensor at which particles from the exhaust gas are accumulated during a measuring phase and the quantity of said particles is determined, and in which the particles are burnt during a heating phase by heating the particle sensor by means of the electric heater.

6. A method for diagnosing the function of a heated exhaust gas sensor in an exhaust gas, wherein the exhaust gas sensor is at least temporarily brought to an operating temperature during a heating phase by heating with an electric heater, comprising determining a necessary heating power (13, 23, 33, 80) for reaching the operating temperature, determining an available heating power (12, 22, 32, 84) for reaching the operating temperature, carrying out a diagnosis for the detection of an intact or defective exhaust gas sensor if the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined threshold value, and not carrying out the diagnosis if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power and the threshold value, wherein when the exhaust gas sensor is not inferred to be faulty, regeneration of the exhaust gas sensor is performed, wherein the necessary heating power (13, 23, 33, 80) is determined from a characteristic diagram at least as a function of an exhaust gas speed (72) and an exhaust gas temperature (71), or in that the necessary heating power (13, 23, 33, 80) is determined from a physical model at least as a function of a thermal conductivity coefficient or a temperature of the exhaust gas sensor or a wall temperature of an exhaust gas duct or the exhaust gas speed (72) or the exhaust gas temperature (71) or a thermal irradiation coefficient, individually in each case or in combination of at least two of the variables, and/or in that the available heating power (12, 22, 32, 84) is determined from an available supply voltage (73) of the heater or from the available supply voltage (73) multiplied by a maximum duty cycle (74) or from a limit, predefined by a control device, of the supply voltage (73).

7. The method according to claim 6, characterized in that the comparison between the available heating power (12, 22, 32, 84) and the necessary heating power (13, 23, 33, 80) is carried out on the basis of a first quotient of the available heating power (12, 22, 32, 84) and the necessary heating power (13, 23, 33, 80) or on the basis of a second quotient (85) of the necessary heating power (13, 23, 33, 80) and the available heating power (12, 22, 32, 84) as a comparison variable, or in that the comparison is carried out on the basis of a first difference (14, 24, 34) between the available heating power (12, 22, 32, 84) and the necessary heating power (13, 23, 33, 80) or on the basis of a second difference between the necessary heating power (13, 23, 33, 80) and the available heating power (12, 22, 32, 84) as a comparison variable.

8. The method according to claim 7, characterized in that during a heating phase or a time segment of the heating phase the minimum first quotient which occurs or the greatest second quotient (86) which occurs or the minimum first difference (14, 24, 34) which occurs or the greatest second difference which occurs is determined, and in that a diagnosis for the detection of an intact or defective exhaust gas sensor is carried out if the minimum first quotient which occurs or the minimum first difference (14, 24, 34) which occurs is greater than a respective predefined value or if the greatest second quotient (86) which occurs or the greatest second difference which occurs is lower than a respective predefined value.

9. The method according to claim 6, characterized in that the available heating power (12, 22, 32, 84) and the necessary heating power (13, 23, 33, 80) are variables.

10. The method according to claim 6, characterized in that a defective exhaust gas sensor is inferred if
   a) during a heating phase a predefined operating temperature is not reached or if the predefined operating temperature is not reached for a predefined time period or if a measuring phase following the heating phase is not started and if
   b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that an intact exhaust gas sensor is inferred if
   a) during a heating phase a predefined operating temperature is reached or if the predefined operating temperature is reached for a predefined time period or if a measuring phase following the heating phase is started and if
   b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that no diagnosis of the exhaust gas sensor takes place if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the predefined threshold value.

11. The method according to claim 6, characterized in that a defective exhaust gas sensor is inferred if
   a) during a heating phase (10, 20, 30) a predefined operating temperature is not reached or if the predefined operating temperature is not reached for a predefined time period or if a measuring phase following the heating phase is not started and if
   b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined first threshold value, and/or
in that an intact exhaust gas sensor is inferred if
   a) during a heating phase a predefined operating temperature is reached or if the predefined operating temperature is reached for a predefined time period or if a measuring phase following the heating phase is started and if
   b) the available heating power (12, 22, 32, 84) during the heating phase was at least temporarily lower than the necessary heating power (13, 23, 33, 80) or if the available heating power (12, 22, 32, 84) during the heating phase was at least temporarily lower than the sum of the necessary heating power (13, 23, 33, 80) and a second threshold value which is lower compared to the first threshold value, and/or
in that no diagnosis of the exhaust gas sensor takes place if
   a) during a heating phase a predefined operating temperature is not reached or if the predefined operating temperature is not reached for a predefined time period or if a measuring phase following the heating phase is not started and if
   b) the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the first threshold value, and/or
in that no diagnosis of the exhaust gas sensor takes place if
   a) during a heating phase a predefined operating temperature is reached or if the predefined operating temperature is reached for a predefined time period or if a measuring phase following the heating phase is started and if
   b) the available heating power (12, 22, 32, 84) during the heating phase was continuously greater than the necessary heating power (13, 23, 33, 80) or if the available heating power (12, 22, 32, 84) during the heating phase was continuously greater than the sum of the necessary heating power (13, 23, 33, 80) and the second threshold value.

12. The method according to claim 6, characterized in that when diagnosis is carried out and an exhaust gas sensor is detected as being defective after a first heating phase, an entry is made in a fault memory, and in that the entry in the fault memory is reached if during a following heating phase a predefined operating temperature is reset and/or if the predefined operating temperature is reached for a predefined time period and/or if a measuring phase following the heating phase is started and if a determined comparative variable during the following heating phase yields a ratio between the necessary heating power (13, 23, 33, 80) and the available heating power (12, 22, 32, 84), which is less favourable compared to the first heating phase.

13. The method according to claim 6, wherein the method is used for monitoring a particle sensor at which particles from the exhaust gas are accumulated during a measuring phase and the quantity of said particles is determined, and in which the particles are burnt during a heating phase by heating the particle sensor by means of the electric heater.

14. The method according to claim 6, characterized in that the available heating power (12, 22, 32, 84) and the necessary heating power (13, 23, 33, 80) are each one of a heater effective voltage, a square of the heater effective voltage, a heater duty cycle or an output heating power is used.

15. A method for diagnosing the function of a heated exhaust gas sensor in an exhaust gas, wherein the exhaust gas sensor is at least temporarily brought to an operating temperature during a heating phase by heating with an electric heater, comprising determining a necessary heating power (13, 23, 33, 80) for reaching the operating temperature, determining an available heating power (12, 22, 32, 84) for reaching the operating temperature, carrying out a diagnosis for the detection of an intact or defective exhaust gas sensor if the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined threshold value, and not carrying out the diagnosis if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power and the threshold value, wherein when the exhaust gas sensor is not inferred to be faulty, regeneration of the exhaust gas sensor is performed, wherein the comparison between the available heating power (12, 22, 32, 84) and the necessary heating power (13, 23, 33, 80) is carried out on the basis of a first quotient of the available heating power (12, 22, 32, 84) and the necessary heating power (13, 23, 33, 80) or on the basis of a second quotient (85) of the necessary heating power (13, 23, 33, 80) and the available heating power (12, 22, 32, 84) as a comparison variable, or in that the comparison is carried out on the basis of a first difference (14, 24, 34) between the available heating power (12, 22, 32, 84) and the necessary heating power (13, 23, 33, 80) or on the basis of a second difference between the necessary heating power (13, 23, 33, 80) and the available heating power (12, 22, 32, 84) as a comparison variable.

16. The method according to claim 15, characterized in that during a heating phase or a time segment of the heating phase the minimum first quotient which occurs or the greatest second quotient (86) which occurs or the minimum first difference (14, 24, 34) which occurs or the greatest second difference which occurs is determined, and in that a diagnosis for the detection of an intact or defective exhaust gas sensor is carried out if the minimum first quotient which occurs or the minimum first difference (14, 24, 34) which occurs is greater than a respective predefined value or if the greatest second quotient (86) which occurs or the greatest second difference which occurs is lower than a respective predefined value.

17. The method according to claim 15, characterized in that the available heating power (12, 22, 32, 84) and the necessary heating power (13, 23, 33, 80) are variables.

18. The method according to claim 15, characterized in that a defective exhaust gas sensor is inferred if
 a) during a heating phase a predefined operating temperature is not reached or if the predefined operating temperature is not reached for a predefined time period or if a measuring phase following the heating phase is not started and if
 b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that an intact exhaust gas sensor is inferred if
 a) during a heating phase a predefined operating temperature is reached or if the predefined operating temperature is reached for a predefined time period or if a measuring phase following the heating phase is started and if
 b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that no diagnosis of the exhaust gas sensor takes place if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the predefined threshold value.

19. The method according to claim 15, characterized in that a defective exhaust gas sensor is inferred if
 a) during a heating phase (10, 20, 30) a predefined operating temperature is not reached or if the predefined operating temperature is not reached for a predefined time period or if a measuring phase following the heating phase is not started and if
 b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined first threshold value, and/or
in that an intact exhaust gas sensor is inferred if
 a) during a heating phase a predefined operating temperature is reached or if the predefined operating temperature is reached for a predefined time period or if a measuring phase following the heating phase is started and if
 b) the available heating power (12, 22, 32, 84) during the heating phase was at least temporarily lower than the necessary heating power (13, 23, 33, 80) or if the available heating power (12, 22, 32, 84) during the heating phase was at least temporarily lower than the sum of the necessary heating power (13, 23, 33, 80) and a second threshold value which is lower compared to the first threshold value, and/or
in that no diagnosis of the exhaust gas sensor takes place if
 a) during a heating phase a predefined operating temperature is not reached or if the predefined operating temperature is not reached for a predefined time period or if a measuring phase following the heating phase is not started and if
 b) the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the first threshold value, and/or
in that no diagnosis of the exhaust gas sensor takes place if
 a) during a heating phase a predefined operating temperature is reached or if the predefined operating temperature is reached for a predefined time period or if a measuring phase following the heating phase is started and if
 b) the available heating power (12, 22, 32, 84) during the heating phase was continuously greater than the necessary heating power (13, 23, 33, 80) or if the available heating power (12, 22, 32, 84) during the heating phase was continuously greater than the sum of the necessary heating power (13, 23, 33, 80) and the second threshold value.

20. The method according to claim 15, characterized in that when diagnosis is carried out and an exhaust gas sensor is detected as being defective after a first heating phase, an entry is made in a fault memory, and in that the entry in the fault memory is reached if during a following heating phase a predefined operating temperature is reset and/or if the predefined operating temperature is reached for a predefined time period and/or if a measuring phase following the heating phase is started and if a determined comparative variable during the following heating phase yields a ratio between the necessary heating power (13, 23, 33, 80) and the available heating power (12, 22, 32, 84), which is less favorable compared to the first heating phase.

21. The method according to claim 15, wherein the method is used for monitoring a particle sensor at which particles from the exhaust gas are accumulated during a measuring phase and the quantity of said particles is determined, and in which the particles are burnt during a heating phase by heating the particle sensor by means of the electric heater.

22. The method according to claim 15, characterized in that the available heating power (12, 22, 32, 84) and the necessary heating power (13, 23, 33, 80) are each one of a heater effective voltage, a square of the heater effective voltage, a heater duty cycle or an output heating power is used.

23. A method for diagnosing the function of a heated exhaust gas sensor in an exhaust gas, wherein the exhaust gas sensor is at least temporarily brought to an operating temperature during a heating phase by heating with an electric heater, comprising determining a necessary heating power (13, 23, 33, 80) for reaching the operating temperature, determining an available heating power (12, 22, 32, 84) for reaching the operating temperature, carrying out a diagnosis for the detection of an intact or defective exhaust gas sensor if the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined threshold value, and not carrying out the diagnosis if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power and the threshold value, wherein when the exhaust gas sensor is not inferred to be faulty, regeneration of the exhaust gas sensor is performed, when diagnosis is carried out and an exhaust gas sensor is detected as being defective after a first heating phase, an entry is made in a fault memory, and in that the entry in the fault memory is reached if during a following heating phase a predefined operating temperature is reset and/or if the predefined operating temperature is reached for a predefined time period and/or if a measuring phase following the heating phase is started and if a determined comparative variable during the following heating phase yields a ratio between the necessary heating power (13, 23, 33, 80) and the available heating power (12, 22, 32, 84), which is less favourable compared to the first heating phase.

24. The method according to claim 23, characterized in that during a heating phase or a time segment of the heating phase the minimum first quotient which occurs or the greatest second quotient (86) which occurs or the minimum first difference (14, 24, 34) which occurs or the greatest second difference which occurs is determined, and in that a diagnosis for the detection of an intact or defective exhaust gas sensor is carried out if the minimum first quotient which occurs or the minimum first difference (14, 24, 34) which occurs is greater than a respective predefined value or if the greatest second quotient (86) which occurs or the greatest second difference which occurs is lower than a respective predefined value.

25. The method according to claim 23, characterized in that the available heating power (12, 22, 32, 84) and the necessary heating power (13, 23, 33, 80) are variables.

26. The method according to claim 23, characterized in that a defective exhaust gas sensor is inferred if
a) during a heating phase a predefined operating temperature is not reached or if the predefined operating temperature is not reached for a predefined time period or if a measuring phase following the heating phase is not started and if
b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that an intact exhaust gas sensor is inferred if
a) during a heating phase a predefined operating temperature is reached or if the predefined operating temperature is reached for a predefined time period or if a measuring phase following the heating phase is started and if
b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by the predefined threshold value, and/or
in that no diagnosis of the exhaust gas sensor takes place if the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the predefined threshold value.

27. The method according to claim 23, characterized in that a defective exhaust gas sensor is inferred if
a) during a heating phase (10, 20, 30) a predefined operating temperature is not reached or if the predefined operating temperature is not reached for a predefined time period or if a measuring phase following the heating phase is not started and if
b) the available heating power (12, 22, 32, 84) during the heating phase was continuously greater than the necessary heating power (13, 23, 33, 80) or if the available heating power (12, 22, 32, 84) during the heating phase was continuously greater than the necessary heating power (13, 23, 33, 80) by a predefined first threshold value, and/or
in that an intact exhaust gas sensor is inferred if
a) during a heating phase a predefined operating temperature is reached or if the predefined operating temperature is reached for a predefined time period or if a measuring phase following the heating phase is started and if
b) the available heating power (12, 22, 32, 84) during the heating phase was at least temporarily lower than the necessary heating power (13, 23, 33, 80) or if the available heating power (12, 22, 32, 84) during the heating phase was at least temporarily lower than the sum of the necessary heating power (13, 23, 33, 80) and a second threshold value which is lower compared to the first threshold value, and/or in that no diagnosis of the exhaust gas sensor takes place if
a) during a heating phase a predefined operating temperature is not reached or if the predefined operating temperature is not reached for a predefined time period or if a measuring phase following the heating phase is not started and if
b) the available heating power (12, 22, 32, 84) during the heating phase was at least temporarily lower than the necessary heating power (13, 23, 33, 80) or if the available heating power (12, 22, 32, 84) was at least temporarily lower than the sum of the necessary heating power (13, 23, 33, 80) and the first threshold value, and/or in that no diagnosis of the exhaust gas sensor takes place if
a) during a heating phase a predefined operating temperature is reached or if the predefined operating temperature is reached for a predefined time period or if a measuring phase following the heating phase is started and if
b) the available heating power (12, 22, 32, 84) during the heating phase was continuously greater than the necessary heating power (13, 23, 33, 80) or if the available heating power (12, 22, 32, 84) during the heating phase was continuously greater than the sum of the necessary heating power (13, 23, 33, 80) and the second threshold value.

28. The method according to claim 23, wherein the method is used for monitoring a particle sensor at which particles from the exhaust gas are accumulated during a measuring phase and the quantity of said particles is determined, and in which the particles are burnt during a heating phase by heating the particle sensor by means of the electric heater.

29. The method according to claim 23, characterized in that the available heating power (12, 22, 32, 84) and the necessary heating power (13, 23, 33, 80) are each one of a heater effective voltage, a square of the heater effective voltage, a heater duty cycle or an output heating power is used.

* * * * *